United States Patent [19]

Wilson

[11] Patent Number: 4,849,012
[45] Date of Patent: Jul. 18, 1989

[54] METHOD FOR GROWING CITRUS FRUITS
[75] Inventor: William C. Wilson, Lakeland, Fla.
[73] Assignee: Teijin Limited, Osaka, Japan
[21] Appl. No.: 223,598
[22] Filed: Jul. 25, 1988
[51] Int. Cl.$^4$ ............................................. A01N 31/00
[52] U.S. Cl. ................................................... 71/122
[58] Field of Search ......................................... 71/122
[56] References Cited
U.S. PATENT DOCUMENTS
4,150,970 4/1979 Bies et al. ............................. 71/122

Primary Examiner—Catherine L. Mills
Attorney, Agent, or Firm—Sughrue, Mion, Zinn, Macpeak and Seas

[57] ABSTRACT

A method for enhancing the sweetness of citrus fruit comprising treating leaves and/or fruit of citrus trees with an effective amount of a dispersion containing 1-triacontanol at least once in the period of from the flowering stage to the harvesting stage, thereby improving the Brix/acid ratio of citrus fruit.

11 Claims, No Drawings

METHOD FOR GROWING CITRUS FRUITS

FIELD OF THE INVENTION

The present invention relates to an improved method for growing citrus fruits. Particularly, the present invention relates to a method for increasing the sweetness of citrus fruits, in other words, improving the Brix/acid ratio, by applying a treating solution containing 1-triacontanol as an active ingredient, to the plants in the period of from the flowering stage to the harvesting stage.

BACKGROUND OF THE INVENTION

Fruits of citrus such as orange, navels and grapefruit contain sugars and citric acid. Their unique saccharinity (sweetness flavor) is basically the total soluble solids of citrus juice (mainly sucrose and other sugars and usually measured with a Brix hydrometer) divided by the total % of acidity (mainly citric and other organic acids) as calculated by titration with standard alkali. The resulting number is called Ratio. Usually, the Brix/acid ratio is used as an index of the sweetness, of citrus fruits and improvement in their sweetness by lowering the acidity and/or increasing the Brix value which result in an increase in this ratio, is desired.

It is known that an arsenic compound, such as sodium arsanilate or lead arsenate, can be used to increase the sweetness of citrus fruits. The use of arsenic compounds has been prohibited since the spring of 1987 in the United States of America, except for extremely limited use, for example, for grapefruit, because these compounds are considered toxic.

SUMMARY OF THE INVENTION

An object of the present invention is to provide a method of increasing the sweetness, namely improving the Brix/acid ratio, of citrus fruits using a treating agent of high safety without any concern as to toxicity.

Another object of the present invention is to provide an easily applicable method of increasing the sweetness, in other words, improving the Brix/acid ratio, of citrus fruits, capable of wide geographic use.

According to the present invention, a method for increasing the sweetness, or improving the Brix/acid ratio, of citrus fruits is provided, the method comprising treating citrus trees, at least the leaves and/or fruit thereof, at least once with a dispersion of an effective amount of 1-triacontanol from the flowering stage to the harvesting period.

DETAILED DESCRIPTION OF THE INVENTION

1-Triacontanol, also known as myricyl alcohol has the formula $CH_3(CH_2)_{28}CH_2OH$ and is a long chain aliphatic alcohol having a molecular weight of 438.83, a melting point of 88° C. and density of 0.777. At room temperature, this compound is a crystalline material, scarcely soluble in water, soluble in alcohol and readily soluble in ether and benzene.

1-Triacontanol is known as a growth regulator for plants, as disclosed in U.S. Pat. No. 4,150,970 which discloses plant growth regulation by application of an aqueous dispersion of 1-triacontanol to the plant.

The present invention involves the discovery that 1-triacontanol increases the sweetness of citrus fruits, when it is applied to citrus trees, at least to the leaves and/or fruits of the trees, in a period from the flowering stage to harvesting stage, preferably from the period of early physiological fruit dropping state (the so-called "June drop") to 3 days before harvesting.

1-Triacontanol used in the present invention is slightly soluble as stated above and cannot be applied to trees in the form of an aqueous solution. Thus, it is employed as an aqueous dispersion, for application to citrus trees. The concentration of 1-triacontanol in the aqueous dispersion is at least $10^{-3}$ ppb, preferably more than $10^{-1}$ ppb. The upper limit of the concentration is not limited, but in general is 100 ppm, preferably 500 ppb, from the standpoint of dispersibility and economy.

The aqueous dispersion of 1-triacontanol is desirably prepared so that the compound is dispersed in the medium as ultrafine particles with very high stability and a variety of dispersing agents can be employed to achieve good dispersion. Further, a variety of wetting agents such as those well known in the art can be used to help spread the compound on the leaves, when 1-triacontanol is applied to the trees. The application of 1-triacontanol in the form of a solid powder or in the form of a solution in a solvent such as an alcohol, benzene or an ether is not desirable, because application of the powder form results in only a slight effect, while use of a solution in a solvent damages the trees or causes a fire hazard.

Suitable dispersing agents which can be used in preparation of the 1-triacontanol dispersion can be selected from one or more of the group consisting of "Tween 20" described in U.S. Pat. No. 4,150,900, sodium octadecyl sulfate,

sodium lauryl sulfate and sodium tallow alkyl sulfate.

1-Triacontanol preferably exists in the aqueous dispersion in the form of fine particles of less than 0.5 μm and preferably ultrafine particles of less than 0.3 μm.

In case of ultrafine particles, the dispersion stability is preferably maintained by using sodium tallow alkyl sulfate, sodium polyoxyethylene sorbitan monolaurate, octadecyl sodium sulfate or a combination thereof. A preferred amount of the emulsifier is no more than 0.1% by weight.

When citrus fruits are grown according to the present invention, the time and the manner of treatment are important.

(a) Time of Treatment:

The dispersion is applied from the flowering stage to the harvesting stage, preferably from the early physiological fruit dropping stage (the so-called "June dropping") to 3 days before harvesting.

The dispersion should be applied at a temperature above 0° C., preferably about 20° C. to 40° C. Application at an extremely low temperature, for example, at the temperature of cool nights in winter, results in very low effectiveness.

(b) Treatment:

At least the leaves and/or fruits of the citrus trees preferably are treated with the 1-triacontanol aqueous dispersion. However, application to only the stems or only the roots of the trees is less effective. In general, application to the trees is done by spraying but other methods can be used.

(c) Effective Amount:

1-Triacontanol provides an adequate effect with use of an extremely small amount. The effective amount depends on the size of the citrus trees, but citrus trees of a typical size in the U.S.A. can be suitably treated with 20 to 50 liters of the aqueous dispersion per tree.

(d) Number of Applications:

The aqueous dispersion is applied at least once and 1-triacontanol is adequately effective even if only a single application is used.

Citrus fruits produced by use of the method of this invention involving treatment with 1-triacontanol have increased sweetness in comparison with untreated fruits. The sweetness is given as the ratio of the sugars to the acids in the fruits, and treatment with 1-triacontanol has been shown to improve this ratio by about 5 to 10%. The optimal combination of citrus species and application conditions have resulted in a 50% improvement.

The present invention can be applied to all types of citrus fruits including oranges, tangelos, navels, lemons, limes, grapefruit or the like and is especially effective on oranges.

The following examples are given to illustrate the present invention in greater detail. However, these examples are not to be construed as limiting the present invention. Unless otherwise indicated herein, all parts, percents, ratios and the like are by weight.

TESTING METHODS AND PROCEDURES (a) Sweetness

Sweetness is defined as a ratio of °Brix to total acid, namely by the ratio=°Brix/total acid.

°Brix means the total soluble solids in the juice of citrus fruits, in other words, a large number of soluble constituents, chiefly sugars, with small amounts of organic acids, vitamins, proteins, free amino acids, essential oils and glucosides. Other compounds are also present in minute quantities. Approximately 85 percent of the total solids are sugars. They are measured in tests by means of a Brix hydrometer. This instrument, which actually measures specific gravity, is calibrated so that degrees Brix, or percent pure sucrose, at a temperature of 20° C. can be read directly.

(b) Total (titratable) Acid

Total acid is measured as described below. Acid in citrus juice is principally citric acid, with smaller amounts of malic, tartaric, and succinic acids also being present. Twenty five cubic centimeters of the same juice used for the Brix test are sampled using a pipette and drained into an Erlenmeyer flask. Three or four drops of phenolphthalein indicator solution are added. A burette is filled with a solution of 0.3125 N sodium hydroxide.

This sodium hydroxide solution is added slowly to the flask with constant agitation until the distinct pink (but not red) endpoint of phenolphthalein is reached.

Although it is universally called "total acid", strictly speaking the amount of acid found by titration should be termed "titratable acid" since additional acid, not ordinarily neutralizable, is actually present in citrus juice.

In maturity testing, acid found by titration is always expressed in terms of percent anhydrous citric acid.

PREPARATION EXAMPLE 1

(Preparation of an aqueous dispersion of 1-triacontanol)

1-Triacontanol (abbreviated "TRIA" hereinafter) was added to water containing 10 ppm of sodium tallow alkyl sulfate dissolved therein and the mixture was treated with ultrasonic waves to form a dispersion. The dispersion was filtered to remove large particles of TRIA whereby a fine particle aqueous dispersion containing about 800 ppm of TRIA was obtained.

The fine particle dispersion was diluted with water to prepare a 0.67 ppb dispersion (designated "Dispersion L") and another 1.33 ppb dispersion (designated "Dispersion H").

Sodium tallow alkyl sulfate has the formula:

$C_nH_{(2n+1)}OSO_3Na$ where the content of n=14 was 3.8%; n=16, 27.9% and n=18, 63.2%.

PREPARATION EXAMPLE 2

(Preparation of an ultrafine dispersion of 1-triacontanol)

Forty milliliters of a 5% aqueous solution of "Tween 20" (polyoxyethylenesorbitan monolaurate) were prepared. Then, the solution was combined with 40 mg of triacontanol and the mixture was subjected to ultrasonic treatment under heating at about 90° C. for 20 minutes. This treatment was stopped for 5 minutes, and then the ultrasonic treatment was further conducted under heating for 10 minutes and for an additional 25 minutes under air-cooling. The evaporated water was replaced to a volume of 40 ml to prepare an ultrafine dispersion of 1,000 ppm triacontanol. The particle size of the dispersion was measured with an N4 Coulter Subcron Particle Analyzer [manufactured by the Coulter Co. (U.S.A.)] and was found to be 70 angstroms on the average.

The resultant dispersion was diluted with water to prepare 2 dispersions of triacontanol concentrations of 4 ppb (Dispersion L') and 100 ppb (Dispersion H'), respectively. EXAMPLE 1

In a citrus grove near Lake Alfred, Fla., U.S.A. where approximately 90 Hamlin orange trees per acre were grown, the trees were sprayed with Dispersion L and Dispersion H using a backpack sprayer under the following conditions:

(a) Application Time:

7 months after bloom; fruit was harvested, 14 days later.

(b) Concentrations and Amounts:

The concentrations were 0.67 ppb (Dispersion L), 1.33 ppb (Dispersion H), respectively, and the dispersion volume applied was 30 liters per tree.

The pH of each dispersion was adjusted to 6-7.

(c) Number of Applications:

One application.

The sweetness of 300 oranges treated with the 0.67 ppb and 1.33 ppb 1-triacontanol dispersions, respectively (total 600), and that of 500 untreated oranges from the same grove were determined and the following results were obtained:

| Dispersion | Concentration (ppb) | Site | Brix | Acid | Ratio (%) | Improvement (%) |
|---|---|---|---|---|---|---|
| L | 0.67 | LA | 9.79 ± 0.07 | 1.2 ± 0.09 | 8.19 ± 0.5 | +9 |

-continued

| Dispersion | Concentration (ppb) | Site | Brix | Acid | Ratio (%) | Improvement (%) |
|---|---|---|---|---|---|---|
| H | 1.33 | LA | 9.61 ± 0.15 | 0.98 ± 0.03 | 9.81 ± 0.39 | +30 |
| — | control | LA | 9.40 ± 0.37 | 1.20 ± 0.04 | 7.53 ± 0.46 | — |

Note:
The term Improvement herein means improvement in the ratio based on the control.

EXAMPLE 2

In a fruit grove near Labelle, Fla., U.S.A. where approximately 25 Hamlin orange trees per acre were grown, the trees were sprayed with Dispersion L and Dispersion H by using a backpack sprayer under the following conditions:

(a) Application Time:

7¼ months after bloom; fruit was harvested 27 days later.

(b) Concentrations, Amounts, pH and Number of Applications:

The concentrations, amounts, pH and the number of applications were the same as described in Example 1.

The sweetness of 400 oranges treated with the 0.67 ppb and 1.33 ppb 1-triacontanol dispersions, respectively (total 800), and 500 untreated oranges from the same grove were determined and the following results were obtained:

| Dispersion | Concentration (ppb) | Site | Brix | Acid | Ratio (%) | Improvement (%) |
|---|---|---|---|---|---|---|
| L | 0.67 | LB | 10.48 ± 0.21 | 0.85 ± 0.02 | 12.35 ± 0.51 | +33 |
| H | 1.33 | LB | 10.39 ± 0.08 | 0.75 ± 0.02 | 13.86 ± 0.43 | +49 |
| — | control | LB | 8.97 ± 0.26 | 0.97 ± 0.03 | 9.30 ± 0.25 | — |

Note:
LB: Labelle.

EXAMPLE 3

In a fruit grove near Labelle, Fla., U.S.A. where approximately 125 Valencia orange trees per acre were grown, the trees were sprayed with Dispersion L' and Dispersion H' using a backpack sprayer under the following conditions:

(a) Application Time:

12¼ months after bloom; fruit was harvested 15 days later.

(b) Concentrations and Amounts:

The concentrations were 4 ppb (Dispersion L') and 100 ppb (Dispersion H'), respectively and 30 liters per tree were applied.

(c) Number of Applications:

Once

The sweetness of 500 oranges treated with the 4 ppb and 100 ppb 1-triacontanol dispersions, respectively, (total 1,000), and that of 800 untreated oranges from the same groove was determined and the following results were obtained:

While the invention has been described in detail and by reference to specific embodiments thereof, various changes and modifications can be made therein without departing from the spirit and scope thereof.

I claim:

1. A method for enhancing the sweetness of fruits comprising treating citrus trees with an effective amount of a dispersion containing 1-triacontanol at least once in the period from the flowering stage to the harvesting stage thereby improving the Brix/acid ratio of the citrus fruits.

2. A method according to claim 1, wherein said method comprises treating the leaves and/or fruit of the citrus trees.

3. A method according to claim 1, wherein the dispersion is an aqueous dispersion containing $10^{-3}$ ppb to 100 ppm of ultrafine particles of 1-triacontanol.

4. A method according to claim 3, wherein the average size of the ultrafine particles is 0.5 μm or less.

5. A method according to claim 1, wherein the dispersion has a pH of from 6 to 7.

6. A method according to claim 1, wherein the method comprises applying the dispersion to the trees in the period from the early physiological fruit dropping state to 3 days before harvesting.

7. A method according to claim 1, wherein the method comprises applying the dispersion at a temperature above 0° C.

8. A method according to claim 3, wherein the dispersion contains a dispersing agent and a wetting agent.

9. A method according to claim 8, wherein the dispersing agent is sodium tallow alkyl sulfate, sodium polyoxyethylene sorbitan monolaurate, octadecyl sodium sulfate or a combination thereof.

10. A method according to claim 8, wherein the amount of the dispersing agent is no more than 0.1% by weight.

11. A method according to claim 1, wherein said citrus trees are orange trees.

* * * * *

| Dispersion | Concentration (ppb) | Site | Brix | Acid | Ratio (%) | Improvement (%) |
|---|---|---|---|---|---|---|
| L' | 4 | LB | 12.36 ± 0.23 | 0.84 ± 0.05 | 14.70 ± 1.04 | +4 |
| H' | 100 | LB | 11.98 ± 0.16 | 0.77 ± 0.06 | 15.66 ± 1.04 | +11 |
| — | control | LB | 12.34 ± 0.68 | 0.88 ± 0.09 | 14.09 ± 1.21 | — |

Note:
LB: Labelle.

UNITED STATES PATENT AND TRADEMARK OFFICE
CERTIFICATE OF CORRECTION

PATENT NO. : 4,849,012

DATED : July 18, 1989

INVENTOR(S) : William C. Wilson

It is certified that error appears in the above-identified patent and that said Letters Patent is hereby corrected as shown below:

Column 2, lines 45-46 delete "sodium polyoxyethylene sorbitan monolaurate, octadecyl sodium sulfate" and insert --polyoxyethylene sorbitan monolaurate, sodium octadecyl sulfate--

Claim 9, delete "sodium polyoxyethylene sorbitan monolaurate" and insert --polyoxyethylene sorbitan monolaurate--

Signed and Sealed this

Twenty-seventh Day of February, 1990

Attest:

JEFFREY M. SAMUELS

Attesting Officer

Acting Commissioner of Patents and Trademarks